(12) United States Patent
Rodriguez et al.

(10) Patent No.: US 11,871,224 B2
(45) Date of Patent: *Jan. 9, 2024

(54) SYSTEM AND METHOD FOR AUTHENTICATING WIRELESS PROGRAMMING SYSTEM AND METHOD FOR AUTHENTICATING WIRELESS PROGRAMMING DEVICES IN PROGRAMMABLE MEDICAL SYSTEMS

(71) Applicant: THE ALFRED E. MANN FOUNDATION FOR SCIENTIFIC RESEARCH, Valencia, CA (US)

(72) Inventors: Saul Rodriguez, Moorpark, CA (US); Dianna (Dan) Han, Valencia, CA (US); Emil Istoc, Winnetka, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/664,411

(22) Filed: May 21, 2022

(65) Prior Publication Data

US 2022/0286849 A1 Sep. 8, 2022

Related U.S. Application Data

(63) Continuation of application No. 17/664,360, filed on May 20, 2022, which is a continuation of application
(Continued)

(51) Int. Cl.
*H04L 29/06* (2006.01)
*H04W 12/06* (2021.01)
(Continued)

(52) U.S. Cl.
CPC ........... *H04W 12/06* (2013.01); *A61B 5/0024* (2013.01); *A61B 5/0031* (2013.01); *A61F 2/72* (2013.01);
(Continued)

(58) Field of Classification Search
CPC ..... H04L 9/3271; H04L 63/061; H04L 67/12; H04L 63/06; H04L 63/0428; H04L 2209/80; H04W 12/04
See application file for complete search history.

(56) References Cited

U.S. PATENT DOCUMENTS

2013/0054467 A1* 2/2013 Dala .................. G06F 21/6245 705/51
2016/0007176 A1* 1/2016 Moisanen .............. H04W 4/90 455/404.1

* cited by examiner

*Primary Examiner* — Evans Desrosiers
(74) *Attorney, Agent, or Firm* — Michael J. Bolan; Vista IP Law Group, LLP

(57) ABSTRACT

A medical device of a medical system is configured for communicating with an external programmer over a wireless communications link. The medical device comprises a wireless communications module configured for receiving a first unencrypted version of a random number and a first encrypted version of the random number from the external programmer over the wireless communications link. The medical device further comprises control circuitry configured for performing an authentication procedure on the external programmer based on the first unencrypted version of the random number and the first encrypted version of the random number, and preventing the external programmer from commanding the medical device to perform an action unless the authentication procedure is successful.

22 Claims, 8 Drawing Sheets

Related U.S. Application Data

No. 16/869,863, filed on May 8, 2020, now Pat. No. 11,375,370, which is a continuation of application No. 15/452,339, filed on Mar. 7, 2017, now Pat. No. 10,652,740.

(60) Provisional application No. 62/304,603, filed on Mar. 7, 2016.

(51) Int. Cl.

| | | |
|---|---|---|
| *H04L 9/32* | (2006.01) | |
| *H04L 67/12* | (2022.01) | |
| *H04L 9/40* | (2022.01) | |
| *H04L 69/40* | (2022.01) | |
| *A61N 1/372* | (2006.01) | |
| *H04L 67/141* | (2022.01) | |
| *H04W 12/50* | (2021.01) | |
| *H04L 67/53* | (2022.01) | |
| *G16H 40/40* | (2018.01) | |
| *A61B 5/00* | (2006.01) | |
| *A61F 2/72* | (2006.01) | |
| *H04Q 9/00* | (2006.01) | |
| *H04W 12/04* | (2021.01) | |
| *G06F 21/62* | (2013.01) | |

(52) U.S. Cl.
CPC ......... *A61N 1/37252* (2013.01); *G16H 40/40* (2018.01); *H04L 9/3271* (2013.01); *H04L 63/061* (2013.01); *H04L 63/0869* (2013.01); *H04L 67/12* (2013.01); *H04L 67/141* (2013.01); *H04L 67/53* (2022.05); *H04L 69/40* (2013.01); *H04Q 9/00* (2013.01); *H04W 12/04* (2013.01); *H04W 12/50* (2021.01); *A61B 5/0004* (2013.01); *G06F 21/6245* (2013.01); *G08C 2201/60* (2013.01); *H04L 63/0428* (2013.01); *H04L 63/06* (2013.01); *H04L 2209/80* (2013.01); *H04L 2209/88* (2013.01); *H04Q 2209/43* (2013.01)

SYSTEM AND METHOD FOR AUTHENTICATING WIRELESS PROGRAMMING SYSTEM AND METHOD FOR AUTHENTICATING WIRELESS PROGRAMMING DEVICES IN PROGRAMMABLE MEDICAL SYSTEMS

RELATED APPLICATION

The present application is a continuation of U.S. patent application Ser. No. 17/664,360, filed May 20, 2022, entitled, "SYSTEM AND METHOD FOR AUTHENTICATING WIRELESS PROGRAMMING DEVICES IN PROGRAMMABLE MEDICAL SYSTEMS," which is a continuation of U.S. patent application Ser. No. 16/869,863, filed May 8, 2020, entitled, "SYSTEM AND METHOD FOR AUTHENTICATING WIRELESS PROGRAMMING DEVICES IN PROGRAMMABLE MEDICAL SYSTEMS," which is a continuation of U.S. patent application Ser. No. 15/452,339, filed Mar. 7, 2017, entitled, "SYSTEM AND METHOD FOR AUTHENTICATING WIRELESS PROGRAMMING DEVICES IN PROGRAMMABLE MEDICAL SYSTEMS," which claims priority from U.S. Provisional Patent Application Ser. No. 62/304,603, filed Mar. 7, 2016, which are expressly incorporated herein by reference.

FIELD OF THE INVENTION

The present invention generally relates to wireless programming techniques in medical systems, and specifically relates to authenticating wireless programming devices, such as clinician programmers, for use in programmable medical systems.

BACKGROUND OF THE INVENTION

Medical systems, such as implantable medical systems, typically comprise one or more implantable medical devices and an external telemetry controller capable of controlling operation of the implanted medical device(s) and acquiring physiological data or operational status data from the implanted medical device(s). Implantable medical systems may further comprise an external programmer, such as a clinician programmer or patient programmer, that may download operating parameters or programs into the telemetry controller to set or otherwise modify the operating configuration of the implantable medical system and/or upload information, such as the physiological data or operational status data, from the telemetry controller.

Communication between such an external programmer and telemetry controller of an implantable medical system may be conveniently accomplished through wireless means, such as radio frequency (RF) communication. One method of wirelessly communicating between an external programmer and a telemetry controller uses a short-range RF communications in accordance with Bluetooth technology. The external programmer and telemetry controller can be paired by exchanging or otherwise storing a shared secret key (referred to as a "link key") that is used to subsequently authenticate the external programmer and encrypt data and commands sent between the external programmer and telemetry controller. Thus, by design, only the external programmer and any previously paired external programmer are permitted to communicate with the telemetry controller.

However, present telemetry controllers that communicate with external programmers over a Bluetooth communications link may be susceptible to inadvertent or intentional hijacking by unauthorized users, because the link key may be surreptitiously acquired or otherwise generated as a default in some operational systems, such as Linux. Once acquired, the shared link key can be used by any device to communication with the telemetry controller. As such, a potential vulnerability from undesired modification of the operating configuration of medical equipment may arise.

There, thus, remains a need for preventing or otherwise deterring unauthorized programming of medical equipment, such as telemetry controllers used in implantable medical systems.

SUMMARY OF THE INVENTION

In accordance with a first aspect of the present inventions, a medical device of a medical system configured for communicating with an external programmer over a wireless communications link (e.g., one having a range of less than one hundred feet) is provided.

The medical device comprises a wireless communications module configured for receiving a first unencrypted version of a random number and a first encrypted version of the random number from the external programmer over the wireless communications link. In one embodiment, the wireless communications module is a radio frequency (RF) communications module, such as one that communicates with the external programmer in accordance with a Bluetooth or a Wi-Fi protocol.

The medical device further comprises control circuitry (e.g., a microcontroller) configured for performing an authentication procedure on the external programmer based on the first unencrypted version of the random number and the first encrypted version of the random number, and preventing the external programmer from commanding the medical device to perform an action (e.g., allowing modification of at least one operational parameter of the medical system) unless the authentication procedure is successful. The wireless communications module may be hardwired to the control circuitry. The wireless communications module may be configured for establishing the wireless communications link with the external programmer by authenticating the external programmer at a first security level, sending status messages to the control circuitry indicating the status of the wireless communications link with the external programmer, in which case, the control circuitry may be configured for performing the authentication procedure at a second security level.

In one embodiment, the control circuitry is configured for performing the authentication procedure by generating a second encrypted version of the random number from the first unencrypted version of the random number, comparing the first and second versions of the encrypted random number, and determining if the first and second versions of the encrypted random number match. In another embodiment, the control circuitry is configured for performing the authentication procedure by decrypting the first encrypted version of the random number to recover a second unencrypted version of the random number, comparing the first and second versions of the unencrypted random number, and determining if the first and second versions of the unencrypted random number match.

The wireless communications module may be configured for receiving a session request from the external programmer over the wireless communications link and sending the session request to the control circuitry, in which case, the control circuitry may be configured for performing the authentication procedure in response to receiving the session request. The control circuitry may be configured for instructing the wireless communications module to send an acknowledge command to the external programmer over the wireless communications link if the authentication procedure is successful, and for instructing the wireless communications module to send a non-acknowledge command to the external programmer over the wireless communications link if the authentication procedure fails.

In one embodiment for preventing the external programmer from commanding the medical device to perform the action, the medical device further comprises a power source configured for supplying power to the wireless communications module, and a wireless actuator configured for being triggered in response to a user action (e.g., a physical wireless actuator, such as a button, configured for being physically triggered in response to the user action), in which case, the control circuitry may be configured for permitting the supply of power from the power source to the wireless communications module in response to the triggering of the wireless actuator, and terminating the supply of power from the power source to the wireless communications module if the authentication procedure is not completed within a predetermined period of time and/or if the authentication procedure fails.

In this embodiment, the medical device may further comprise a switch coupled between the power source and the wireless communications module, in which case, the control circuitry may be configured for permitting the supply of power from the power source to the wireless communications module by closing the switch, and for terminating the supply of power from the power source to the wireless communications module by opening the switch. The control circuitry may comprise a timer configured for being started in response to the triggering of the wireless actuator, and for being stopped if the authentication procedure succeeds. The control circuitry may be configured for opening the switch if the timer indicates that the predetermined period of time has elapsed.

In another embodiment, the control circuitry is configured for preventing the external programmer from commanding the medical device to perform the action by instructing the wireless communications module to not forward commands received from the external programmer over the wireless communications link to the control circuitry. In still another embodiment, the wireless communications module is configured for forwarding commands received from the external programmer over the wireless communications link to the control circuitry, and the control circuitry is configured for preventing the external programmer from commanding the medical device to perform the action by ignoring the commands forwarded from the wireless communications module. In yet another embodiment, the control circuitry is configured for preventing the external programmer from commanding the medical device to perform the action by instructing the wireless communications module to terminate the wireless communication link.

In one specific embodiment, the medical device further comprises an external telemetry controller comprising the wireless communications module, the control circuitry, and telemetry circuitry configured for wirelessly communicating with at least one implantable medical device. In this case, the implantable medical device(s) may be configured for sensing physiological data of a patient, and the telemetry circuitry may be configured for wirelessly receiving the physiological data sensed by the implantable medical device(s). The medical device may comprise a prosthesis, and a prosthetic controller electrically coupled to the external telemetry controller for receiving the physiological data, and for controlling the bionic prosthesis based on the physiological data. The prosthesis may be, e.g., a bionic limb, the sensed physiological data is electromyogram (EMG) data, and the prosthetic controller may be configured for controlling movement of the bionic limb based on the sensed EMG data.

In accordance with a second aspect of the present inventions, a medical system comprises an external programmer configured for storing a first encryption algorithm, generating a first unencrypted version of the random number, encrypting the first unencrypted version of the random number in accordance with the first encryption algorithm to generate a first encrypted version of the random number, and transmitting the first unencrypted version of the random number and the first encrypted version of the random number over a wireless communication link (e.g., an RF communications link, such as, e.g., a Bluetooth or a Wi-Fi communications link, such as one in the range of less than one hundred feet).

The medical system further comprises a medical device configured for storing one of a second encryption algorithm that is identical to the first encryption algorithm, and a decryption algorithm that is complementary to the first encryption algorithm, receiving the first unencrypted version of the random number and the first encrypted version of the random number over a wireless communication link (e.g., an RF communications link, such as, e.g., a Bluetooth or a Wi-Fi communications link, such as one in the range of less than one hundred feet), performing an authentication procedure on the external programmer by applying the one of the second encryption algorithm and a decryption algorithm to the first unencrypted version of the random number and the first encrypted version of the random number, and preventing the external programmer from commanding the medical device to perform an action (e.g., allowing modification of at least one operational parameter of the medical system) unless the authentication procedure is successful. The medical device may be configured for establishing the wireless communications link with the external programmer by authenticating the external programmer at a first security level, and for performing the authentication procedure at a second security level.

In one embodiment, the medical device is configured for performing the authentication procedure by generating a second encrypted version of the random number from the first unencrypted version of the random number, comparing the first and second versions of the encrypted random number, and determining if the first and second versions of the encrypted random number match. In another embodiment, the medical device is configured for performing the authentication procedure by decrypting the first encrypted version of the random number to recover a second unencrypted version of the random number, comparing the first and second versions of the unencrypted random number, and determining if the first and second versions of the unencrypted random number match.

The external programmer may be configured for sending a session request over the wireless communication link, in which case, the medical device may be configured for receiving a session request over the wireless communications link, and for performing the authentication procedure in response to receiving the session request. The medical device may be configured for sending an acknowledge command over the wireless communications link if the authentication procedure is successful, and the external programmer may be configured for receiving the acknowledge command over the wireless communications link, and in response to receiving the acknowledge command, sending commands over the wireless communications link to command the medical device to perform the action. The medical device may be configured for sending a non-acknowledge command over the wireless communications link if the authentication procedure fails, and the external programmer may be configured for receiving the non-acknowledge command over the wireless communications link.

In one embodiment for preventing the external programmer from commanding the medical device to perform the action, the medical system further comprises a wireless communications module configured for establishing the wireless communication link, and a wireless actuator configured for being triggered in response to a user action (e.g., a physical wireless actuator, such as a button, configured for being physically triggered in response to the user action), in which case, the medical device may be configured for turning on the wireless communications module in response to the triggering of the wireless actuator, and turning off the wireless communications module if the authentication procedure is not completed within a predetermined period of time and/or if the authentication procedure fails.

In another embodiment for preventing the external programmer from commanding the medical device to perform the action, the external programmer is configured for sending commands to the medical device over the wireless communications link, and the medical device is configured for preventing the external programmer from commanding the medical device to perform the action by ignoring the commands received from the external programmer over the wireless communications link. In still another embodiment, the medical device is configured for preventing the external programmer from commanding the medical device to perform the action by terminating the wireless communications link.

In one specific embodiment, the medical system further comprises at least one implantable medical device, and the medical device further comprises an external telemetry controller configured for wirelessly communicating with the implantable medical device(s). In this case, the implantable medical device(s) may be configured for sensing physiological data of a patient, and the telemetry controller may be configured for wirelessly receiving the physiological data sensed by the implantable medical device(s). The medical system may further comprise a prosthesis, and a prosthetic controller electrically coupled to the external telemetry controller for receiving the physiological data, and for controlling the bionic prosthesis based on the physiological data. The prosthesis may be, e.g., a bionic limb, the sensed physiological data is electromyogram (EMG) data, and the prosthetic controller may be configured for controlling movement of the bionic limb based on the sensed EMG data.

In accordance with a third aspect of the present inventions, a method of communicating between a medical device and an external programmer of a medical system over a wireless communications link (e.g., an RF communications link, such as, e.g., a Bluetooth or a Wi-Fi communications link, such as one in the range of less than one hundred feet) is provided. The method comprises receiving a first unencrypted version of a random number and a first encrypted version of the random number from the external programmer over the wireless communications link, performing an authentication procedure on the external programmer based on the first unencrypted version of the random number and the first encrypted version of the random number, and preventing the external programmer from commanding the medical device to perform an action (e.g., allowing modification of at least one operational parameter of the medical system) unless the authentication procedure is successful. The method may further comprise establishing the wireless communications link between the medical device and external programmer by authenticating the external programmer at a first security level, in which case, the authentication procedure may be performed at a second security level.

One method further comprises storing a first encryption algorithm at the external programmer, generating the first unencrypted version of the random number, encrypting the first unencrypted version of the random number in accordance with the first encryption algorithm to generate the first encrypted version of the random number, transmitting the first unencrypted version of the random number and the first encrypted version of the random number over the wireless communication link, and storing one of a second encryption algorithm identical to the first encryption algorithm and a decryption algorithm complementary to the first encryption algorithm at the medical device.

In this case, the authentication procedure may be performed on the external programmer by respectively applying the second encryption algorithm or the decryption algorithm to the first unencrypted version of the random number or the first encrypted version of the random number. For example, the authentication procedure may be performed by generating a second encrypted version of the random number from the first unencrypted version of the random number, comparing the first and second versions of the encrypted random number, and determining if the first and second versions of the encrypted random number match. As another example, the authentication procedure is performed by decrypting the first encrypted version of the random number to recover a second unencrypted version of the random number, comparing the first and second versions of the unencrypted random number, and determining if the first and second versions of the unencrypted random number match.

Another method further comprises receiving a session request from the external programmer over the wireless communications link, in which case, the authentication procedure may be performed in response to receiving the session request. This method may further comprise sending an acknowledge command to the external programmer over the wireless communications link if the authentication procedure is successful, and in response to receiving the acknowledge command, sending commands from the external programmer to the medical device over the wireless communications link to command the medical device to perform the action. The method may further comprise sending a non-acknowledge command to the external programmer over the wireless communications link if the authentication procedure fails.

One method for preventing the external programmer from commanding the medical device to perform the action comprises receiving a trigger signal in response to a user action, turning on a wireless communications module in response to the trigger signal, establishing the wireless communications link with the wireless communications module, and turning off the wireless communications module if the authentication procedure is not completed within a predetermined period of time and/or if the authentication procedure fails. Another method for preventing the external programmer from commanding the medical device to perform the action comprises sending commands from the external programmer to the medical device over the wireless communications link, and ignoring the commands received from the external programmer over the wireless communications link. In still another method for preventing the external programmer form commanding the medical device to perform the action comprises terminating the wireless communications link.

In accordance with a fourth aspect of the present inventions, a medical device of a medical system configured for communicating with an external programmer over a wireless communications link (e.g., one having a range of less than one hundred feet) is provided. The medical device comprises a wireless communications module configured for establishing a wireless communications link (e.g., one having a range of less than one hundred feet) with the external programmer. In one embodiment, the wireless communications module is a radio frequency (RF) communications module, such as one that communicates with the external programmer in accordance with a Bluetooth or a Wi-Fi protocol.

The medical device further comprises a power source configured for supplying power to the wireless communications module, a wireless actuator configured for being triggered in response to a user action (e.g., a physical wireless actuator, such as a button, configured for being physically triggered in response to the user action), and control circuitry (e.g., a microcontroller) is configured for permitting the supply of power from the power source to the wireless communications module in response to the triggering of the wireless actuator, for performing an authentication procedure on the external programmer, and for terminating the supply of power to the wireless communications module if the authentication procedure is not completed within a predetermined period of time. The wireless communications module may be hardwired to the control circuitry. The wireless communications module may be configured for establishing the wireless communications link with the external programmer by authenticating the external programmer at a first security level, and the control circuitry may be configured for performing the authentication procedure at a second security level.

In one embodiment, the medical device further comprises a switch coupled between the power source and the wireless communications module, and the control circuitry is configured for permitting the supply of power from the power source to the wireless communications module by closing the switch, and for terminating the supply of power from the power source to the wireless communications module by opening the switch. The control circuitry may comprise a timer configured for being started in response to the triggering of the wireless actuator, and for being stopped if the authentication procedure succeeds. The control circuitry may be configured for opening the switch if the timer indicates that the predetermined period of time has elapsed. The control circuitry may be configured for preventing the external programmer from commanding the medical device to perform the action by terminating the supply of power from the power source to the wireless communications module if the authentication procedure fails.

In one specific embodiment, the medical device further comprises an external telemetry controller comprising the wireless communications module, the control circuitry, and telemetry circuitry configured for wirelessly communicating with at least one implantable medical device. In this case, the implantable medical device(s) may be configured for sensing physiological data of a patient, and the telemetry circuitry may be configured for wirelessly receiving the physiological data sensed by the implantable medical device(s). The medical device may comprise a prosthesis, and a prosthetic controller electrically coupled to the external telemetry controller for receiving the physiological data, and for controlling the bionic prosthesis based on the physiological data. The prosthesis may be, e.g., a bionic limb, the sensed physiological data is electromyogram (EMG) data, and the prosthetic controller may be configured for controlling movement of the bionic limb based on the sensed EMG data.

In accordance with a fifth aspect of the present inventions, a medical system comprises an external programmer configured for sending authentication information over a wireless communication link (e.g., an RF communications link, such as, e.g., a Bluetooth or a Wi-Fi communications link, such as one in the range of less than one hundred feet), a medical device, a wireless actuator configured for being triggered in response to a user action (e.g., a physical wireless actuator, such as a button, configured for being physically triggered in response to the user action), and a wireless communications module configured for establishing the wireless communication link between the external programmer and the medical device.

The medical device is configured for turning on the wireless communications module in response to the triggering of the wireless actuator, for performing an authentication procedure on the external programmer based on the authentication information sent by the external programmer, and for turning off the wireless communications module if the authentication procedure is not completed within a predetermined period of time. The medical device may be configured for establishing the wireless communications link with the external programmer by authenticating the external programmer at a first security level, and the medical device may be configured for performing the authentication procedure at a second security level. In one embodiment, the external programmer is configured for programming the medical device, and the medical device is configured for preventing the external programmer from commanding the medical device by turning off the wireless communications module if the authentication procedure fails.

In one specific embodiment, the medical system further comprises at least one implantable medical device, and the medical device further comprises an external telemetry controller configured for wirelessly communicating with the implantable medical device(s). In this case, the implantable medical device(s) may be configured for sensing physiological data of a patient, and the telemetry controller may be configured for wirelessly receiving the physiological data sensed by the implantable medical device(s). The medical system may further comprise a prosthesis, and a prosthetic controller electrically coupled to the external telemetry controller for receiving the physiological data, and for controlling the bionic prosthesis based on the physiological data. The prosthesis may be, e.g., a bionic limb, the sensed physiological data is electromyogram (EMG) data, and the prosthetic controller may be configured for controlling movement of the bionic limb based on the sensed EMG data.

In accordance with a sixth aspect of the present inventions, a method of communicating between a medical device and an external programmer of a medical system over a wireless communications link is provided. The method comprises receiving a trigger signal in response to a user action, turning on a wireless communications module in response to the trigger signal, establishing the wireless communications link with the wireless communications module, and preventing the external programmer from commanding the medical device by turning off the wireless communications module if the external programmer is not authenticated within a predetermined period of time. The method may further comprise receiving authentication information from the external programmer, and authenticating the external programmer based on the received authentication information. The method may further comprise establishing the wireless communications link between the medical device and external programmer by authenticating the external programmer at a first security level, and the external programmer is further authenticated at a second security level.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
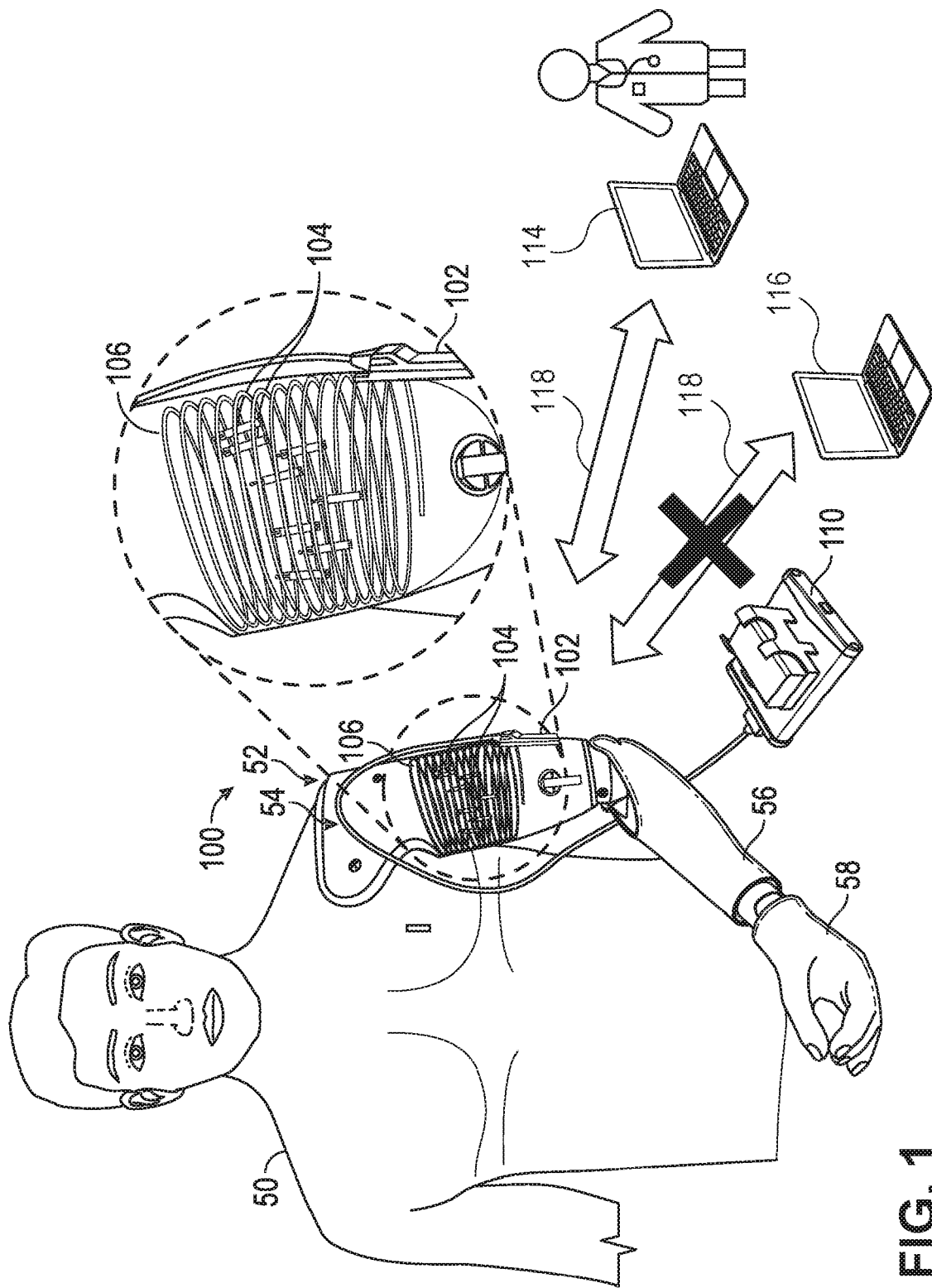
FIG. 1 is a pictorial of a prosthetic control system constructed in accordance with one embodiment of the present inventions.

Referring to FIG. 1, an implantable medical system 100 constructed in accordance with one embodiment of the present inventions will now be described. The implantable medical system 100 generally comprises an external telemetry controller (TC) 102 and a plurality of implantable medical devices 104. In the illustrated embodiment, the implantable medical system 100 takes the form of a prosthetic control system.

In this case, the implantable medical devices 104 may take the form of sensor devices that are implanted within a residual portion of an amputated limb 52 of a patient 50 respectively adjacent muscles of interest for detecting muscle contraction, for example, by monitoring electromyogram (EMG) signals of the muscles of interest. The prosthetic control system 100 comprises a bionic prosthesis 54 having a robotic forearm 56 and robotic hand 58. The TC 102 may be incorporated into the bionic prosthesis 54, and is configured for delivering power to and receiving EMG data from the sensor devices 104. To facilitate power transfer and communications, the TC 102 comprises a primary coil 106, which may be incorporated into the socket portion of the bionic prosthesis 54 in a manner that it surrounds the sensor devices 104 implanted within the residual limb portion 52 of the patient 50. The TC 102 comprises power transfer and communication circuitry (described in further detail below) that inductively powers and communicates with the implanted sensor devices 104 via the primary coil 106.

The prosthetic control system 100 further comprises a prosthetic controller 110 coupled to the TC 102 via a cable 112 for receiving EMG data from TC 102, and is further coupled to motors (not shown) in the bionic prosthesis 54 to control movement of the robotic arm 56 and robotic hand 58. The prosthetic controller 110 may be worn by the patient 50, e.g., on the waist. The prosthetic control system 100 may further comprises one or more batteries (not shown), which may be physically integrated into the prosthesis 54 or otherwise contained in the prosthetic controller 110, for providing power to the circuitry within the TC 102 and prosthetic controller 110.

Thus, the prosthetic control system 100 allows the patient 50 to control the bionic forearm 56 and robotic hand 58 by attempting to contract the muscles in the residual limb portion 52. Different muscles or different portions of the muscles would correspond to independently movable parts, such as the elbow, wrist, and fingers of the bionic prosthesis 54. When a sensor device 104 detects contraction in a muscle or portion of a muscle, it communicates the resulting EMG data to the prosthetic controller 110 via the TC 102 that the muscle or portion of a muscle was contracted. The EMG data identifies the muscle that has been contracted, as well as the magnitude of the contraction. The prosthetic controller 110 then controls the bionic prosthesis 54 to move the independently movable part that corresponds with the muscle that was contracted according to the magnitude of the contraction.

Although the TC 102 and prosthetic controller 110 are shown as being separate physical units in FIG. 1, it should be appreciated that the TC 102 and prosthetic controller 110 may be integrated into a single physical unit that is incorporated into the prosthesis 54 or otherwise worn by the patient 50. It should also be appreciated that although the prosthetic control system 100 has been described as being a prosthetic control system, the prosthetic control system 100 can be any medical system that performs a diagnostic or therapeutic function. Likewise, although the implantable medical devices 102 are described as being EMG sensors, the implantable medical devices 102 may take the form of any medical device that performs a diagnostic or therapeutic function. Furthermore, although the TC 102 is described herein as being external to the patient 50, it should be appreciated that the TC 102 may take the form of, or otherwise be incorporated into, an implantable device that communicates with the other sensor devices 104.

Each of the sensor devices 104 may take the form of a miniaturized cylindrical sensing device, with the circuitry being implemented as a sub-assembly on a single-chip integrated circuit mounted on a ceramic substrate sandwiched between two halves of a cylindrical magnetic core around which the inductive coil is wound. The electronics are encapsulated in a cylindrical ceramic package that include two metal endcaps at opposite ends of the ceramic package that serve as the differential recording electrodes. Such an implantable sensor device allows the EMG signals to be detected at the implantation site of this device. An example of such an implantable sensor device 104 is the IMES® device manufactured by Alfred Mann Foundation and described in Implantable Myoelectric Sensors (IMESs) for Intramuscular Electromyogram Recording, IEEE Trans Biomed Eng. 2009 January, pp. 159-171. In an alternative embodiment, the sensor device 104 may include a lead (not shown) on which the electrodes are carried, so that EMG signals can be detected at a location remote from the implantation site of the body of the device.

The prosthetic control system 100 further comprises a clinician programmer (CP) 114 configured for being operated by a clinician to program the prosthetic controller 110 and/or sensor devices 14 via the TC 102. In the illustrated embodiment, the CP 114 takes the form of a personal computer (PC), although in alternative embodiments, the CP 114 may take the form of a conventional Smartphone configured with a smartphone application with programming capabilities. As will be described in further detail below, the TC 102 and the CP 114 both comprise wireless communication interfaces (e.g., Bluetooth interfaces) that allow the CP 114 to send commands to the prosthetic controller 110 via the TC 102, e.g., for modifying or selecting programs, within the prosthetic controller 110, thereby modifying the operating configuration of the prosthetic control system 100.

Although a third-party device 116 may potentially modify the operating configuration of the prosthetic control system 100 by sending commands to the TC 102 that would modify operational parameters within the sensor devices 104 and/or prosthetic controller 110, the prosthetic control system 100 prevents, or at least minimizes, the chance that a third-party device 116 modifies the operating configuration of the prosthetic control system 100 by preventing the third-party device 116 from sending commands to the TC 102 or otherwise ignoring such commands.

As illustrated in FIG. 1, the TC 102 and CP 114 are configured for communicating with each other over a wireless communications link 118. The wireless communications link 118 is a short-range radio frequency (RF) communications link. In the illustrated embodiment, the RF communications link 118 is a point-to-point communications link, since it is desirable that prosthetic controller 110 be programmed by only one CP 114 at a time, and that the CP 114 program only one prosthetic controller 110 at a time, although there may be some scenarios where it may be desirable to program multiple prosthetic controllers 110 at the same time, in which case, the RF communications link 118 may be a point-to-multiple communications link.

In the illustrated embodiment described herein, the RF communications link 118 is established in accordance with a Bluetooth protocol, although in alternative embodiments, the RF communications link 118 may be established in accordance with other short-range RF protocols, such as a Wi-Fi protocol. The Bluetooth protocol is essentially a detailed specification for short-range (e.g., less than one hundred feet) wireless communications using the unlicensed industry, scientific, and medical (ISM) 2.4 GHz radio band. Bluetooth technology is fundamentally a cable replacement system that provides a universal mechanism for a variety of devices in various configuration that includes a master (in this case, the CP 114) and at least one slave (in this case, the TC 102). The master is defined as the device that initiates the connection procedure to establish the wireless communications link.

Prior to exchanging data, in accordance with the Bluetooth protocol, the CP 114 and telemetry controller 102 establish a relationship between each other via a process called "pairing." The process of pairing the CP 114 and the TC 102 is aimed at creating a shared secret between the devices, referred to as a "Link Key," which is then used to authenticate the CP 114 and TC 102 to each other and encrypt data exchanged between these devices.

The CP 114 initiates the pairing process, which generally has a searching phase and a pairing phase. During the searching phase, the CP 114 identifies all available telemetry controllers (one being the TC 102), each of which responds with its own unique address. The CP 114 reports and stores the unique addresses received from the telemetry controllers. If the telemetry controller 110 is not found in the search results, the search process can be repeated. If the telemetry controller 110 is found in the search results, the clinician programmer 102 initiates the pairing phase to establish the RF communications link 118 with the telemetry controller 110.

The security modes during the pairing process defined by Bluetooth specification range from requiring no encryption or authentication to requiring encryption with authentication. However, regardless of the security procedures used during the pairing process, any device that acquires a shared Link Key can connect and exchange data with the corresponding device with which the Link Key is shared.

To further ensure that the TC 102 only communicates with the clinician programmer 114, rather than the third-party device 116, the prosthetic control system 100 employs additional authentication protocols, and in particular, employs a multi-level authentication process that minimizes the risk that the prosthetic controller 110 is commanded by devices other than the CP 114, thereby avoiding undesired or intended modifications in the operating configuration of the prosthetic control system 100.

To this end, in addition to the Bluetooth pairing protocol, which may or may not include authentication, the prosthetic control system 100 employs a proprietary authentication procedure, coupled with a manually activated wireless communication initiation safeguard, to ensure that the TC 102 can only be programmed or otherwise manipulated by the CP 114.

In particular, the prosthetic control system 100 comprises a wireless actuator 120 configured for being manually triggered in response to user action. In response to triggering of the wireless actuator 120, wireless communication between the TC 102 and the CP 114 is enabled. That is, without manually triggering the wireless actuator 120, wireless communication between the TC 102 and CP 114 is impossible. The wireless actuator 120 may be a physical wireless actuator, e.g., a button that can be pushed, or alternatively can be an electronic or virtual wireless actuator, e.g., an icon on a computer screen, that can be clicked. To ensure that the wireless actuator 120 cannot be triggered via a wireless attack from a third party, the wireless actuator 120 is hardwired to the TC 102. In the illustrated embodiment, the wireless actuator 120 is located on the prosthetic controller 100 and is hardwired to the TC 102 via the cable 112, although the wireless actuator 120 may be located anywhere on, or otherwise in association with, the prosthetic control system 100, including on the TC 102 itself, that allows the wireless actuator 120 to enable wireless communication via a hardwired connection.

In the illustrated embodiment, the wireless communication between the TC 102 and the CP 114 is manually enabled in response to triggering the wireless actuator 120 by turning on a wireless communications module 168 (illustrated in FIG. 2), e.g., by supplying power to the wireless communications module 168. In the embodiment described herein, the wireless communications module 168 is an RF communications module, and in particular, a Bluetooth-compatible module, although other types of RF modules, such as WiFi-compatible modules, can be used.

The Bluetooth module 168 may be automatically turned off (i.e., without user intervention) if a device (presumably, the third-party device 116) is not authenticated to the TC 102 within a predetermined period of time after the wireless actuator 120 has been triggered (e.g., sixty seconds), thereby preventing any devices from initiated wireless communication with, and subsequently commanding, the TC 102. Reasons for not authenticating a device to the TC 102 within the predetermined period of time include, but are not limited to, failure to initiate or establish the wireless communications link 118 in accordance with the Bluetooth protocol, failure to initiate or complete the proprietary authentication procedure, completion of the proprietary authentication procedure with a single failure, completion of the proprietary authentication with multiple failures, etc.

In an alternative embodiment, the Bluetooth module 168 may be turned off if the wireless communications link 118 has not been initiated or otherwise established in accordance with the Bluetooth protocol within a predetermined period of time after the wireless actuator 120 has been triggered (e.g., sixty seconds), or if a device (presumably, the third-party device 116) is not authenticated in accordance with the proprietary authentication procedure (e.g., failure to initiate or complete the proprietary authentication procedure, completion of the proprietary authentication procedure with one or more failures, etc.) within a predetermined period of time (e.g., sixty seconds) after the wireless communications link 118 has been established in accordance with the Bluetooth protocol.

Thus, it can be appreciated from the foregoing that authentication of the CP 114 to the TC 102 and subsequent communication therebetween can only be performed in a very limited period of time that is controlled by the clinician. As such, any third-party device 116 attempting to be authenticated by the TC 102 will have a very limited window of opportunity to do so. It should be appreciated that by requiring the wireless actuator 120 to be manually triggered each time an authentication procedure fails, any attempt by the third-party device 116 of cracking the proprietary encryption/decryption algorithms by repeatedly and quickly generating different unencrypted and encrypted versions of random numbers will be thwarted. Furthermore, turning the Bluetooth module 168 on only when wireless communication with the CP 114 is intended by the clinician has the added benefit of conserving battery power.

In another alternative embodiment, instead of turning the Bluetooth module 168 off if the aforementioned wireless communication conditions are not met within a predetermined period of time, the Bluetooth module 168 can be left on, but instructed to only establish the wireless communication link 118 in accordance with the Bluetooth protocol within a predetermined period of time (e.g., sixty seconds) after the wireless actuator 120 is triggered. For example, the Bluetooth module 168 can be instructed to only accept a request to connect from a device during such predetermined period of time, and reject any request to connect from a device outside of this predetermined period of time. In such a case, if the wireless communications link 118 has been established in accordance with the Bluetooth protocol within the predetermined period of time after the wireless actuator 120 is triggered, the Bluetooth module 168 may be instructed to terminate the wireless communications link 118 if a device (presumably, the third-party device 116) is not authenticated in accordance with the proprietary authentication procedure within a predetermined period of time after the wireless actuator 120 is triggered, or alternatively, if the device is not authenticated in accordance with the proprietary authentication procedure within a predetermined period of time after the wireless communications link 118 has been established in accordance with the Bluetooth protocol.

In still another embodiment, instead of turning off the Bluetooth module 168 or otherwise terminating the wireless communications link 118, any commands sent over the wireless communications link 118 can simply be ignored if a device (presumably, the third-party device 116) is not authenticated in accordance with the proprietary authentication procedure within a predetermined period of time after the wireless actuator 120 is triggered, or alternatively, if the device is not authenticated in accordance with the proprietary authentication procedure within a predetermined period of time after the wireless communications link 118 has been established in accordance with the Bluetooth protocol.

As briefly discussed above, the prosthetic control system 100 performs a proprietary authentication procedure to ensure that the TC 102 can only be programmed or otherwise manipulated by the CP 114. In contrast, to the Bluetooth pairing protocol, which is performed at the physical layer or data layer of the Open Systems Interconnection (OSI) model, the proprietary authentication procedure is performed at the session layer of the OSI model. Thus, the CP 114 is authenticated at a first security level by the Bluetooth pairing protocol, and then further authenticated at a second security level by the proprietary authentication procedure.

To this end, both the TC 102 and CP 114 are installed with proprietary encryption and/or decryption algorithms that are not accessible to the public. These proprietary encryption and/or decryption algorithms are applied to random numbers (e.g., 16 bytes or 128 bits long) to authenticate the CP 114 to the TC 102. In particular, the CP 114 generates a first unencrypted version of a random number, encrypts the first unencrypted version of a random number to generate a first encrypted version of the random number, and transmits both the first unencrypted version of the random number and the first encrypted version of the random number over the wireless communications link 118 previously established between the TC 102 and the CP 114 in accordance with the Bluetooth protocol. The CP 114 receives the first unencrypted version of the random number and the first encrypted version of the random number over the established wireless communications link 118, and performs an authentication procedure based on the first unencrypted version of the random number and the first encrypted version of the random number.

In one embodiment, the TC 110 performs the authentication procedure by encrypting the first unencrypted version of the random number to generate a second encrypted version of the random number, comparing the first and second encrypted versions of the random number, and determining if the first and second encrypted versions of the random number match. Because the encryption algorithm employed by the TC 110 is the same encryption algorithm employed by the CP 114, a match between the first and second encrypted versions of the random number confirms that the CP 114, and not some other third-party device 116, is connected to the TC 110 over the established wireless communications link 118.

In another embodiment, the TC 110 performs the authentication procedure by decrypting the first encrypted version of the random number to recover a second unencrypted version of the random number, comparing the first and second unencrypted versions of the random number, and determining if the first and second unencrypted versions of the random number match. Because the decryption algorithm employed by the TC 110 is complementary to the encryption algorithm employed by the CP 114, a match between the first and second unencrypted versions of the random number confirms that the CP 114, and not some other third-party device 116, is connected to the TC 110 over the established wireless communications link 118.

The TC 102 permits the CP 114 to command the prosthetic controller 110 to perform an action only if the authentication procedure succeeds, i.e., if there is a match between the first and second encrypted versions of the random number or between the first and second unencrypted versions of the random number. For example, the TC 102 may send an acknowledge command to the CP 114 that the authentication procedure is successful, thereby prompting the CP 114 to send commands to the TC 102 and/or passing any commands received from the CP 114 to the prosthetic controller 110.

In contrast, if the authentication procedure fails, i.e., if there is a no match between the first and second encrypted versions of the random number or between the first and second unencrypted versions of the random number, the TC 102 presumes that the wireless communications link 118 has not been established with the CP 114, but rather a third-party device 116, and as such, prevents the third-party device 116 from commanding the TC 102 to perform an action. For example, the supply of power to the Bluetooth module 168 may be terminated, thereby terminating the wireless communications link 118 between the TC 102 and third-party device 116. Alternatively, rather than terminating the wireless communications link 118, if the authentication procedure fails, the TC 102 does not send an acknowledge command to the third-party device 116, thereby preventing the CP 114 from sending commands to the TC 102, or alternatively, the TC 102 may simply ignore commands sent from the CP 114 over the established wireless communications link 118 or refuse to send such commands to the telemetry controller 110.

Figure 2:
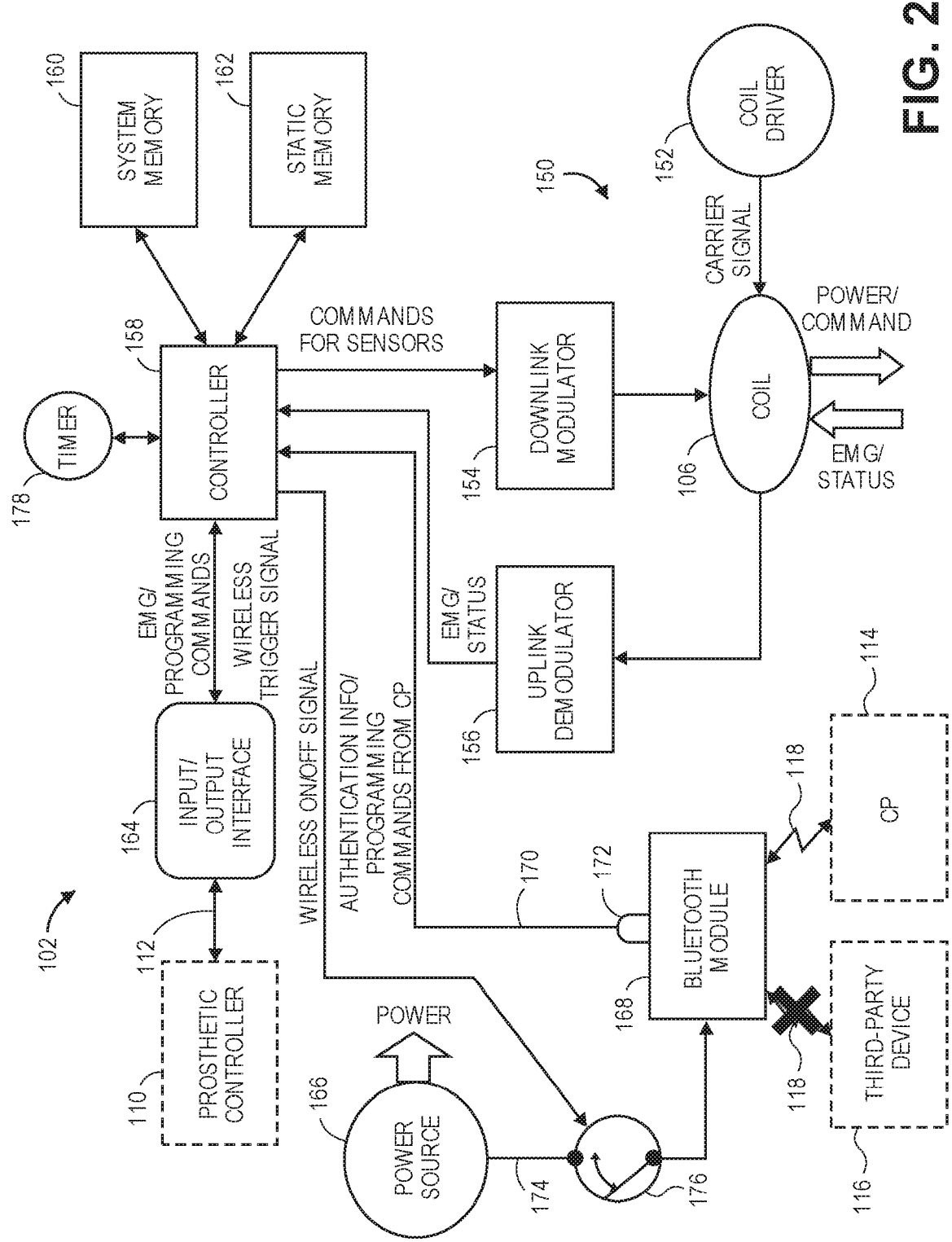
FIG. 2 is a block diagram of one embodiment of the telemetry controller used in the prosthetic control system of FIG. 1.

Referring now to FIG. 2, the TC 102 comprises telemetry/power circuitry 150 configured for transmitting commands and power to the sensor devices 104 and receiving EMG signals or status signals from the sensor devices 104. To this end, the telemetry/power circuitry 150 comprises the aforementioned primary coil 106 and a coil driver 152 configured for applying the primary carrier signal to the primary coil 106, thereby inducing secondary carrier signals on secondary coils (not shown) of the sensor devices 104.

The primary carrier signal is utilized as both a source of power for the sensor devices 104, as well as a downlink/uplink carrier signal for transmitting data and commands between the TC 102 and the sensor devices 104. To this end, the telemetry/power circuitry 150 further comprises a downlink modulator 154 configured for load modulating the primary carrier signal envelope on the primary coil 106 in accordance with command data, thereby inducing an amplitude modulation of the secondary signal envelopes on the secondary coils of the respective sensor devices 104, and allowing the sensor devices 104 to acquire the command data. The telemetry/power circuitry 150 further comprises an uplink demodulator 156 configured for demodulating the primary signal envelope on the primary coil 106 to acquire the EMG data (or status data) from the sensor devices 104. Further details describing techniques for wirelessly communicating between the TC 102 and sensor devices 104 are provided in U.S. Patent Application Ser. No. 62/456,576, entitled "Multiple Implant Communications with Adjustable Load Modulation Based on Received Signal Amplitudes", and U.S. patent application Ser. No. 15/907,457, entitled "Multiple Implant Communications with Adjustable Load Modulation Using Modulation Indices", which are expressly incorporated herein by reference.

The TC 102 further comprising a controller 158 (e.g., a microcontroller), system memory 160 (e.g., RAM), and a static storage device 162 (e.g., ROM or a disk drive). The microcontroller 158 may execute sequences of one or more instructions contained in the system memory 160 for controlling and operating the TC 102, and processing the EMG data received from the sensor device 104. Such instructions may be read into system memory 160 from another computer readable/usable storage medium, such as the static storage device 162. In addition to programs and other data needed to implement the basic operations of the CP 114, the static storage device 162 stores the unique address of the CP 114 (once paired), a communications driver software module (not shown) that implements the portion of the proprietary authentication protocol performed by the TC 102, as described in further detail below, and a command packet parser software module for processing commands received from the CP 114 and sending them to the prosthetic controller 110 or sensor devices 104.

The TC 102 further comprises an input/output interface 164, such as a USB port, for communicating the processed EMG data to, and receiving commands to control the sensor devices 104, from the prosthetic controller 110 via the cable 112. The TC 102 further comprises a power source 166, e.g., a battery, for providing power to the circuitry of the TC 102. The power source 166 may be located in the TC 102, or may be located in the prosthetic controller 110, in which case, power will be provided from the prosthetic controller to the TC 102 via the cable 112.

The TC 102 further comprises the aforementioned Bluetooth module 168 configured for establishing the RF communications link 118 with the CP 114. The TC 102 is configured for transmitting and receiving messages, data, and commands via the Bluetooth module 168 over the established RF communications link 118. The microcontroller 158 is hardwired to the Bluetooth module 168 via a line 170 that is connected to a communication port 172 (e.g., a Universal Asynchronous Receiver/Transmitter (UART) port), thereby allowing the microcontroller 158 and the Bluetooth module 168 to securely message each other. The communications driver software module executed by the microcontroller 158 may be a conventional UART communications driver software module modified to implement the proprietary authentication procedure. Power from the power source 162 is supplied to the Bluetooth module 168 via a dedicated power conduit 174.

The TC 102 further comprises a switch 176 in the conduit 174 configured for being alternately opened and closed under control of the microcontroller 158, thereby selectively supplying or terminating power to the Bluetooth module 168. In the illustrated embodiment, the conduit 174 is dedicated to the Bluetooth module 168, such that the opening or closing of the switch 176 only affects the supply of power from the power source 162 to the Bluetooth module 168, and does not affect the power status of the remaining components to which power is supplied from the power source 162.

The TC 102 further comprises a timer 178 that may be internal or external to the microcontroller 158. In response to manual triggering of the wireless actuator 120, which is securely hardwired to the microcontroller 158 via the cable 112, a signal is sent from the wireless actuator 120 to the microcontroller 158, which in turn, responds by starting the timer 178 and closing the switch 176 to initiate the supply of power from the power source 162 to the Bluetooth module 168. The microcontroller 158 is configured for opening the switch 176 to terminate supply of the power from the power source 166 to the Bluetooth module 168 if the CP 114 has not been authenticated prior to the expiration of the predetermined time of the timer 178. In an alternative embodiment, the timer 178 may be semi-autonomous in nature in that, without intervention by the microcontroller 158, will open the switch 176 to turn off the Bluetooth module 168 once a predetermined period of time (e.g., sixty seconds) has expired.

Figure 3:
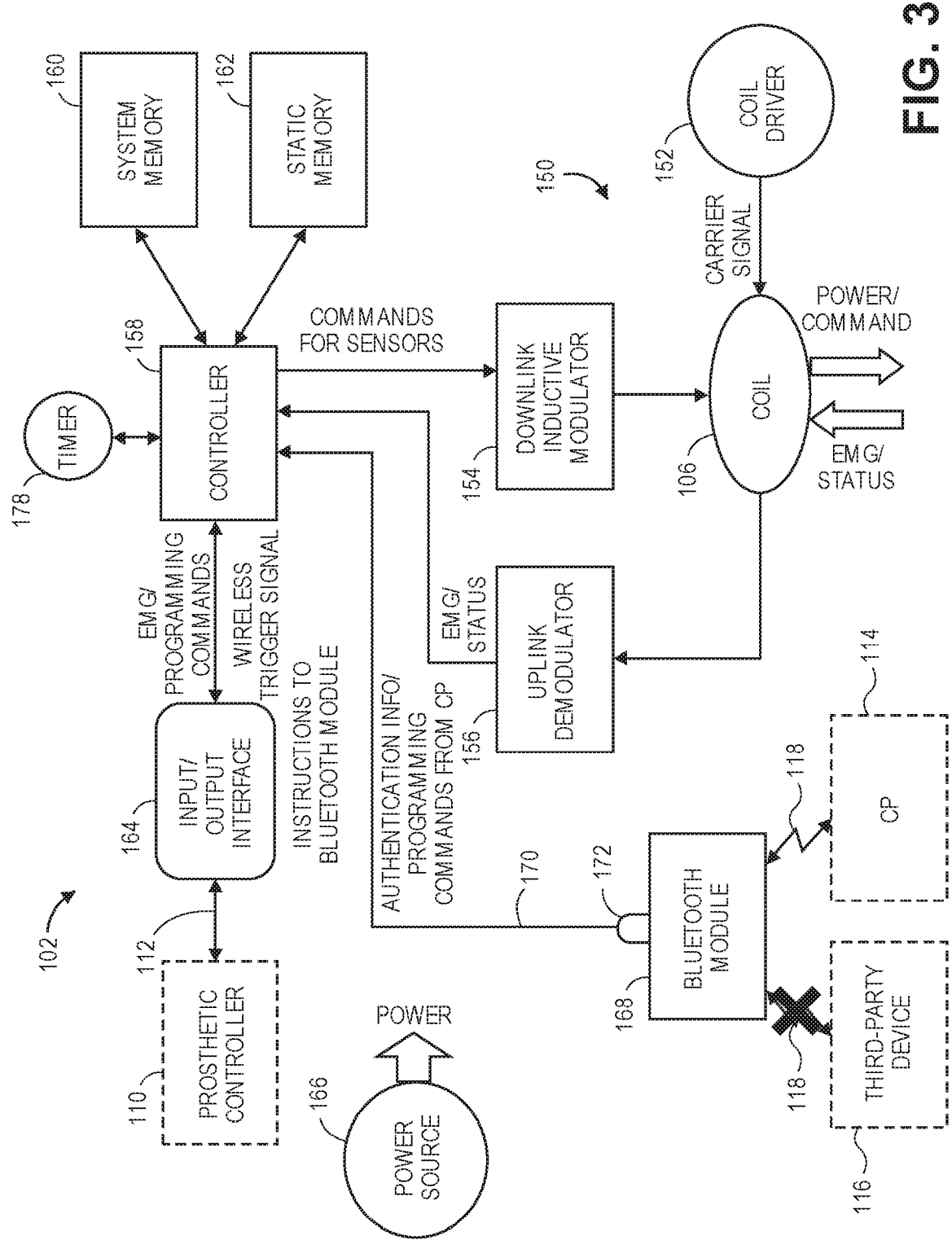
FIG. 3 is a block diagram of another embodiment of the telemetry controller used in the prosthetic control system of FIG. 1.

Thus, as will be described in further detail below, after non-authentication of the third-party wireless device 116, wireless communication between the TC 102 and the non-authenticated third-party device 116 is disabled by opening the switch 176 to turn the Bluetooth module 168 off. Alternatively, as illustrated in FIG. 3, instead of turning the Bluetooth module 168 off to disable wireless communication between the TC 102 and the non-authenticated third-party device 116, the microcontroller 158 instructs the Bluetooth module 168 to not establish the wireless communications link 118 between the TC 102 and the non-authenticated third-party device 116, or if wireless communications link 118 between the TC 102 and the third-party device 116 has already been establishing, the microcontroller 158 instructs the Bluetooth module 168 to terminate the wireless communication link 118 between the TC 102 and the non-authenticated third-party device 116, or alternatively, the microcontroller 158 simply ignores any commands received from the non-authenticated third-party device 116 over the wireless communications link 118.

Figure 4:
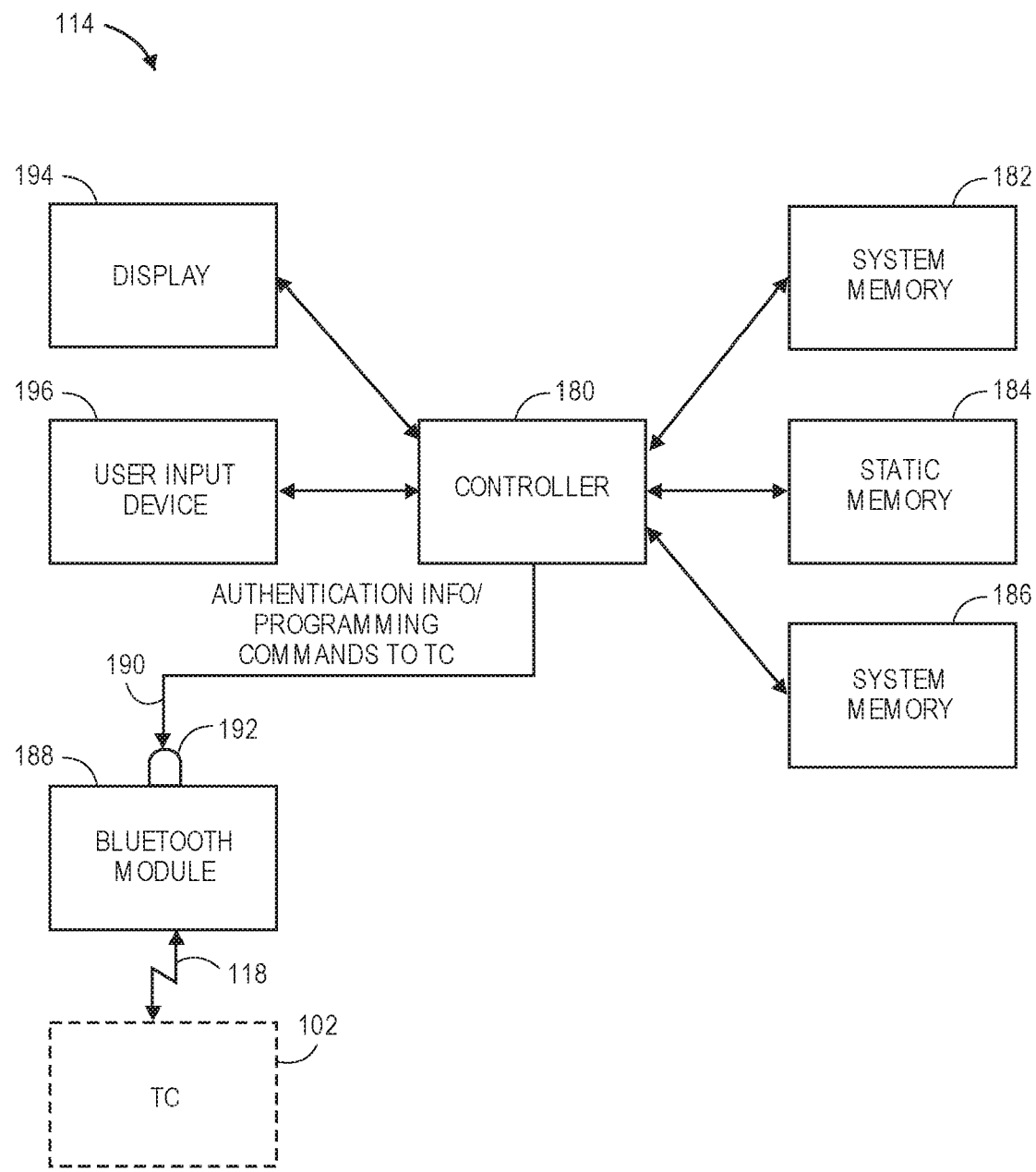
FIG. 4 is a block diagram of a one embodiment of a clinician programmer used in the prosthetic control system of FIG. 1.

Referring now to FIG. 4, the CP 114 comprises a controller 180, system memory 182 (e.g., RAM), a static storage device 184, and a disk drive 186 (e.g., magnetic or optical). The controller 180 may execute sequences of one or more instructions contained in the system memory 182. Such instructions may be read into system memory 182 from another computer readable/usable storage medium, such as static storage device 184 or disk drive 186. In addition to programs and other data needed to implement the basic operations of the CP 114, the static storage device 184 and/or disk drive 186 stores the unique address of the TC 102 (once paired) and a communications driver software module that implements the portion of the proprietary authentication protocol performed by the CP 114, as described in further detail below.

The CP 114 further comprises a wireless communication module 188 that complements the Bluetooth module 168 of the TC 102 to establish the RF communications link 118. In the illustrated embodiment, the wireless communication module 188 is an RF communications module, and in particular, a Bluetooth compatible module. The CP 114 may transmit and receive messages, data, and commands via the Bluetooth module 188 over the established RF communications link 118. The controller 180 is hardwired to the Bluetooth module 188 via a line 190 that is connected to a communication port 192 (e.g., a Universal Asynchronous Receiver/Transmitter (UART) port), thereby allowing the controller 180 and the Bluetooth module 188 to securely message each other. The communications driver software module may be a conventional UART communications driver software module modified to implement the proprietary authentication procedure. The CP 114 further comprises display 194 (e.g., LRT or LCD) and a user input device 196 (e.g., keyboard and cursor control device).

Figure 5A:
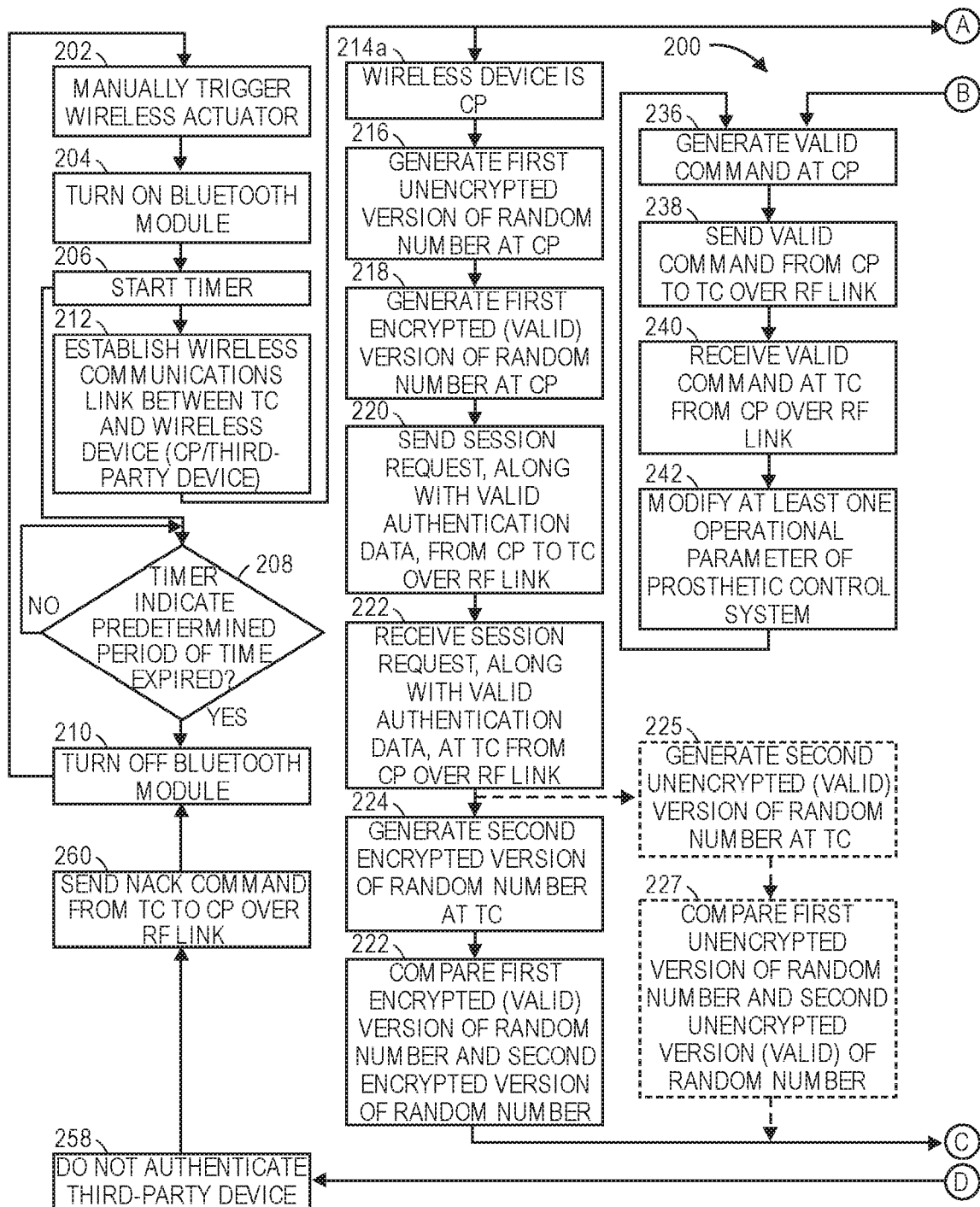
FIGS. 5a and 5b is a flow diagram of illustrating one method of operating the telemetry controller of FIG. 2 to perform an authentication procedure on a wireless device, and preventing the wireless device from commanding the telemetry controller unless the authentication procedure is completed with a successful result.
Figure 5B:
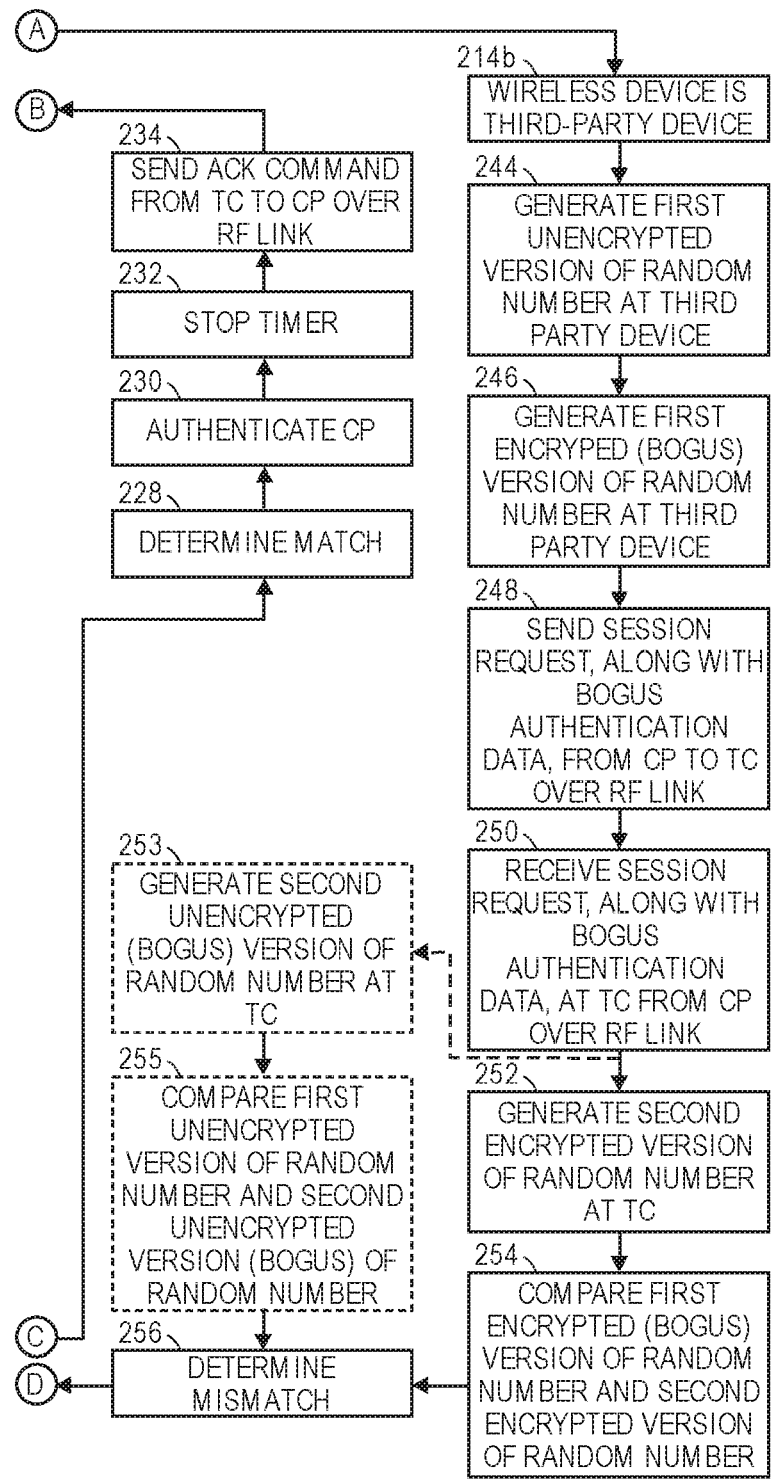

Having described the structure and operation of the prosthetic control system 100, one method 200 of authenticating a wireless device to the TC 102 will now be described with reference to FIGS. 2, 4, and 5. In this method, it is assumed that a wireless device (whether the CP 114 or the third-party device 116) establishes a wireless communications link with the TC 102, and is authenticated and therefore permitted to command the TC 102 if the wireless device is the CP 114, and not authenticated and therefore prohibited from commanding the TC 102 if the wireless device is the third-party device 116.

First, the user (presumably, the clinician) manually triggers the wireless actuator 120 (step 202), and in response, the Bluetooth module 158 is turned on (step 204), and the timer 178 is started (step 206). In the illustrated embodiment, in response to the manual triggering of the wireless actuator 220, a trigger signal is sent from the wireless actuator 120 to the microcontroller 158 of the TC 102, the communication driver software module executed by the microcontroller 158 turns on the Bluetooth module 158 by closing the switch 176 in the conduit 174, thereby supplying power from the power source 166 to the Bluetooth module 168, and starts the timer 178. In an alternative embodiment, the microcontroller 158 may be bypassed, in which case, the trigger signal, itself, directly closes the switch 176 and starts the timer 178.

If at any time during the method 200, the timer 178 indicates that a predetermined period of time (e.g., sixty seconds) has elapsed (step 208), the Bluetooth module 158 is turned off (step 210). In the illustrated embodiment, the communications driver software module executed by the microcontroller 158 of the TC 102 turns off the Bluetooth module 158 by opening the switch 176 in the conduit 174, thereby terminating the supply of power from the power source 166 to the Bluetooth module 168. The timer 178 may be repeatedly monitored by the microcontroller 158 of the TC 102 (e.g., once a second) during the method 200 to determine whether the predetermined period of time has elapsed. In an alternative embodiment, the microcontroller 158 may be bypassed, in which case, the timer 178, itself, may directly open the switch 176 when the period of time has elapsed. At any time during the method 200, including after the Bluetooth module 168 has been turned off, the user may manually trigger the wireless actuator 120 at step 202 to turn the Bluetooth module 168 back on.

As long as the Bluetooth module 168 remains turned on, the RF communications link 118 between the TC 102 and the wireless device (either the CP 114 or the third-party device 116) may be established in accordance with the Bluetooth protocol (step 212). For example, if the wireless device has not been previously paired, using the wireless device as the master device, a user (presumably, but not necessarily, the clinician) may search for all available Bluetooth devices on the wireless device, each of which responds with its own unique address. The wireless device reports and stores the unique address received from the TC 102. If the TC 102 is not found in the search results, the search process can be repeated. If the TC 102 is found in the search results, the user may then click on the specific TC 102 in the list of available Bluetooth devices displayed on the wireless device, thereby initiating pairing process. The wireless device will then be paired by generating a shared Link Key (with or without authentication), and the RF communications link 118 will then be subsequently established therebetween. Such process may or may not require the entry of a passcode into the wireless device.

If the TC 102 and wireless device have already been previously paired, they may automatically establish the RF communications link 118 therebetween if, e.g., the TC 102 was the last Bluetooth device to which the wireless device was last connected, or if the TC 102 was not the last Bluetooth device to which the wireless device was last connected, the clinician may click on the specific TC 102, which will be indicated as being paired in the list of available Bluetooth devices displayed on the wireless device, thereby establishing the RF communications link 118 therebetween. It should be appreciated that establishing the RF communication link 118 between the TC 102 and a wireless device in accordance with the Bluetooth protocol is well-known and the details will not be described herein for purposes of brevity.

Once the RF communications link 118 has been established between the TC 102 and the wireless device (either the CP 114 or the third-party device 116), the TC 102 performs an authentication procedure on the wireless device.

In particular, if the wireless device is the CP 114 (step 214a), the controller 180 of the CP 114 executes the communications driver software module that implements the proprietary encryption algorithm to generate a first unencrypted version of a random number (step 216), and to encrypt the first unencrypted version of the random number to generate a first encrypted (valid) version of the random number (step 218). The controller 180 then instructs the Bluetooth module 188 to send a start session request, along with the valid authentication information (i.e., the first unencrypted version of the random number and the first encrypted (valid) version of the random number), over the established RF communications link 118 (step 220). The Bluetooth module 168 of the TC 102 receives the start session request, along with the valid authentication information (i.e., the first unencrypted version of the random number and the first encrypted (valid) version of the random number), over the established RF communications link 118, and sends this information to the microcontroller 158 (step 222).

The microcontroller 158 of the TC 102 then performs an authentication procedure on the CP 114 based on the first unencrypted version of the random number and the first encrypted (valid) version of the random number. In particular, the communications driver software module executed by the microcontroller 158 of the TC 102 implements the proprietary encryption algorithm to encrypt the first unencrypted version of the random number received from the CP 114 to generate a second encrypted version of the random number (step 224), and to compare the first encrypted (valid) version of the random number received from the CP 114 to the second encrypted version of the random number (step 226).

Alternatively, the communications driver software module executed by the microcontroller 158 of the TC 102 implements the proprietary encryption algorithm that is complementary to the proprietary encryption algorithm used by the CP 114 to decrypt the first encrypted (valid) version of the random number received from the CP 114 to generate a second unencrypted (valid) version of the random number (step 225), and compares the first unencrypted version of the random number received from the CP 114 to the second unencrypted (valid) version of the random number (step 227).

The communication driver software module executed by the microcontroller 158 then determines that there is a match between the first encrypted (valid) version of the random number received from the CP 114 to the second encrypted version of the random number (i.e., the first encrypted (valid) version of the random number is identical to the second encrypted version of the random number), or alternatively, that there is a match between the first unencrypted version of the random number received from the CP 114 to the second unencrypted (valid) version of the random number (i.e., the first unencrypted version of the random number is identical to the second unencrypted (valid) version of the random number) (step 228). In response to the match, the communication driver software module executed by the microcontroller 158 then deems the authentication procedure to be successful and authenticates the CP 114 (step 230), stops the timer 178 (step 232), and instructs the Bluetooth module 158 to send an acknowledgment (ACK) command over the RF communications link 118 to the CP 114 (step 234).

In response to receiving the ACK command from the TC 102, the controller 180 of the CP 114 generates a valid command (step 236), and the communications driver software module executed by the controller 180 instructs the Bluetooth module 188 of the CP 114 to send the valid command to the TC 102 over the RF communications link 118 (step 238). The Bluetooth module 168 of the TC 102 receives the valid commands over the established RF communications link 118, and sends these commands to the microcontroller 158 (step 240). In response to receiving the valid commands, the microcontroller 158 performs an action, and in the illustrated embodiment, allows modification of at least one operational parameter of the prosthetic control system 100 (step 242). In particular, the microcontroller 158 executes the command packet parser software module, and the communications driver software module passes the valid command to the command packet parser software module, which processes and sends the valid command to the prosthetic controller 110 via the cable 112 to modify operational parameter(s) in the prosthetic controller 110, or to the sensor devices 104 via the telemetry circuitry 150 to modify operational parameter(s) within the sensor devices 104. Steps 236-242 can be repeated to generate and act on additional valid commands.

In the case where the RF communications link 118 is established at step 212 by the third-party device 116 (step 214b), the third-party device 116 may attempt to emulate the proprietary encryption algorithm to generate a first unencrypted version of a random number (step 244), and to encrypt the first unencrypted version of the random number to generate a first encrypted (bogus) version of the random number (step 246). The third-party device 116 then sends a start session request, along with the bogus authentication information (i.e., the first unencrypted version of the random number and the first encrypted (bogus) version of the random number), over the established RF communications link 118 (step 248). The Bluetooth module 168 of the TC 102 receives the start session request, along with the bogus authentication information (i.e., the first unencrypted version of the random number and the first encrypted (bogus) version of the random number, over the established RF communications link 118, and sends this information to the microcontroller 158 (step 250).

The microcontroller 158 then performs an authentication procedure on the third-party device 116 based on the first unencrypted version of the random number and the first encrypted (bogus) version of the random number. In particular, the communications driver software module executed by the microcontroller 158 of the TC 102 implements the proprietary encryption algorithm to encrypt the first unencrypted version of the random number received from the third-party device 116 to generate a second encrypted version of the random number (step 252), and to compare the first (bogus) encrypted version of the random number received from the third-party device 116 to the second encrypted version of the random number (step 254).

Alternatively, the communications driver software module executed by the microcontroller 158 of the TC 102 implements the proprietary encryption algorithm that is complementary to the proprietary encryption algorithm used by the third-party device 116 to decrypt the first encrypted (bogus) version of the random number received from the third-party device 116 to generate a second unencrypted (bogus) version of the random number (step 253), and compare the first unencrypted version of the random number received from the third-party device 116 to the second unencrypted (bogus) version of the random number (step 255).

The communication driver software module executed by the microcontroller 158 then determines that there is a mismatch between the first encrypted (bogus) version of the random number received from the third-party device 116 to the second encrypted version of the random number (i.e., the first encrypted (bogus) version of the random number is not identical to the second encrypted version of the random number), or alternatively, that there is a mismatch between the first unencrypted version of the random number received from the third-party device 116 and the second unencrypted (bogus) version of the random number (i.e., the first unencrypted version of the random number is not identical to the second unencrypted (bogus) version of the random number) (step 256).

In response to the mismatch, the communication driver software module executed by the microcontroller 158 then deems the authentication procedure to be a failure and does not authenticate the third-party device 116 (step 258), instructs the Bluetooth module 158 to send a non-acknowledgment (NACK) command over the RF communications link 118 to the TC 102 (step 260), and turns off the Bluetooth module 168 by opening the switch 176 in the conduit 174, thereby terminating the supply of power from the power source 166 to the Bluetooth module 168 (step 210). The clinician will then have to manually trigger the wireless actuator 120 again in order to turn the Bluetooth module 158 back on and attempt another authentication of the CP 114 to the TC 102. Alternatively, instead of turning off the Bluetooth module 168, the method may return to step 244 where the third-party device 116 may attempt to be authenticated again. In such a case, attempted authentication of the third-party device 116 may be repeated until the timer 178 indicates that the predetermined period of time has expired at step 208.

Figure 6A:
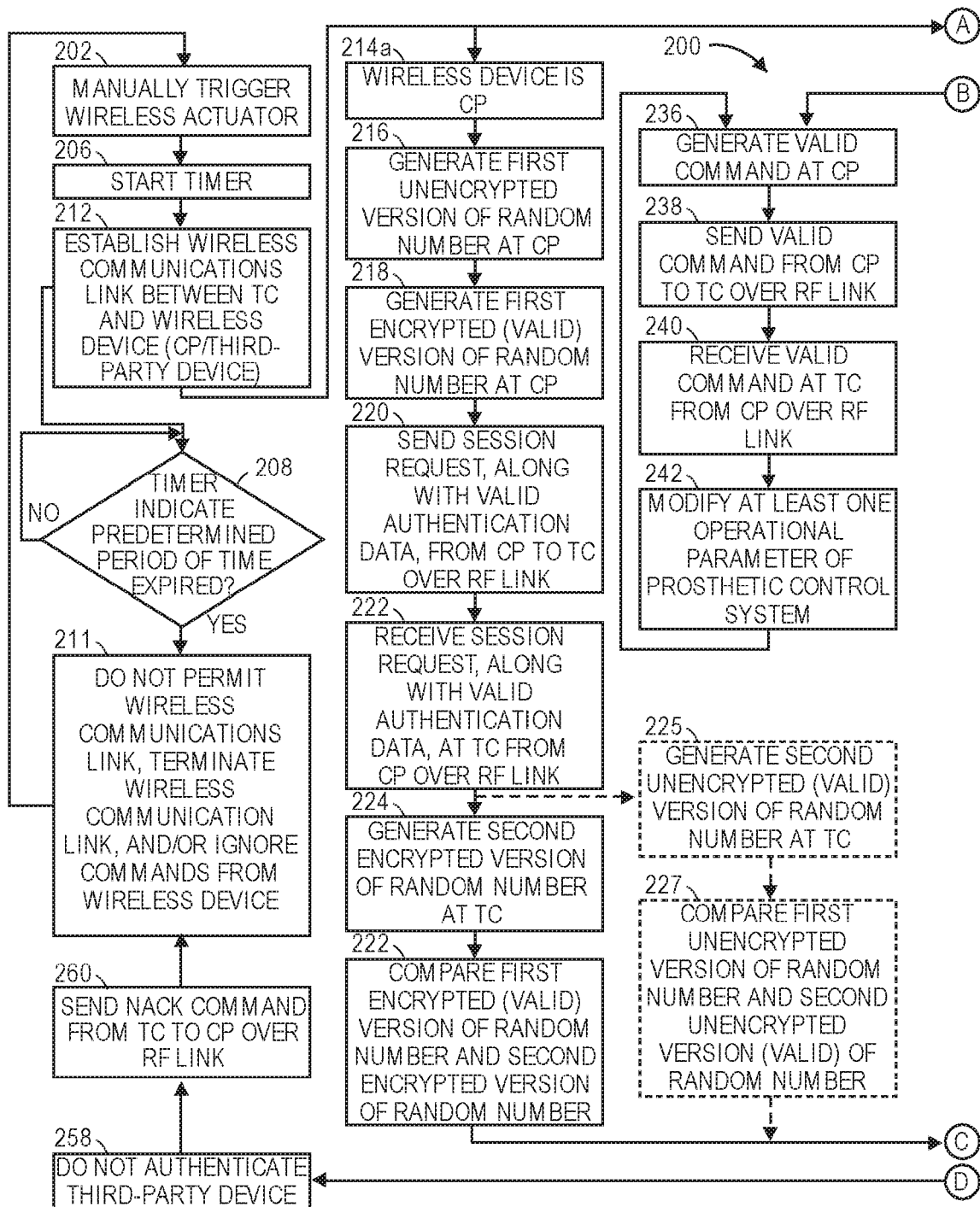
FIGS. 6a and 6b is a flow diagram of illustrating one method of operating the telemetry controller of FIG. 3 to perform an authentication procedure on a wireless device, and preventing the wireless device from commanding the telemetry controller unless the authentication procedure is completed with a successful result.
Figure 6B:
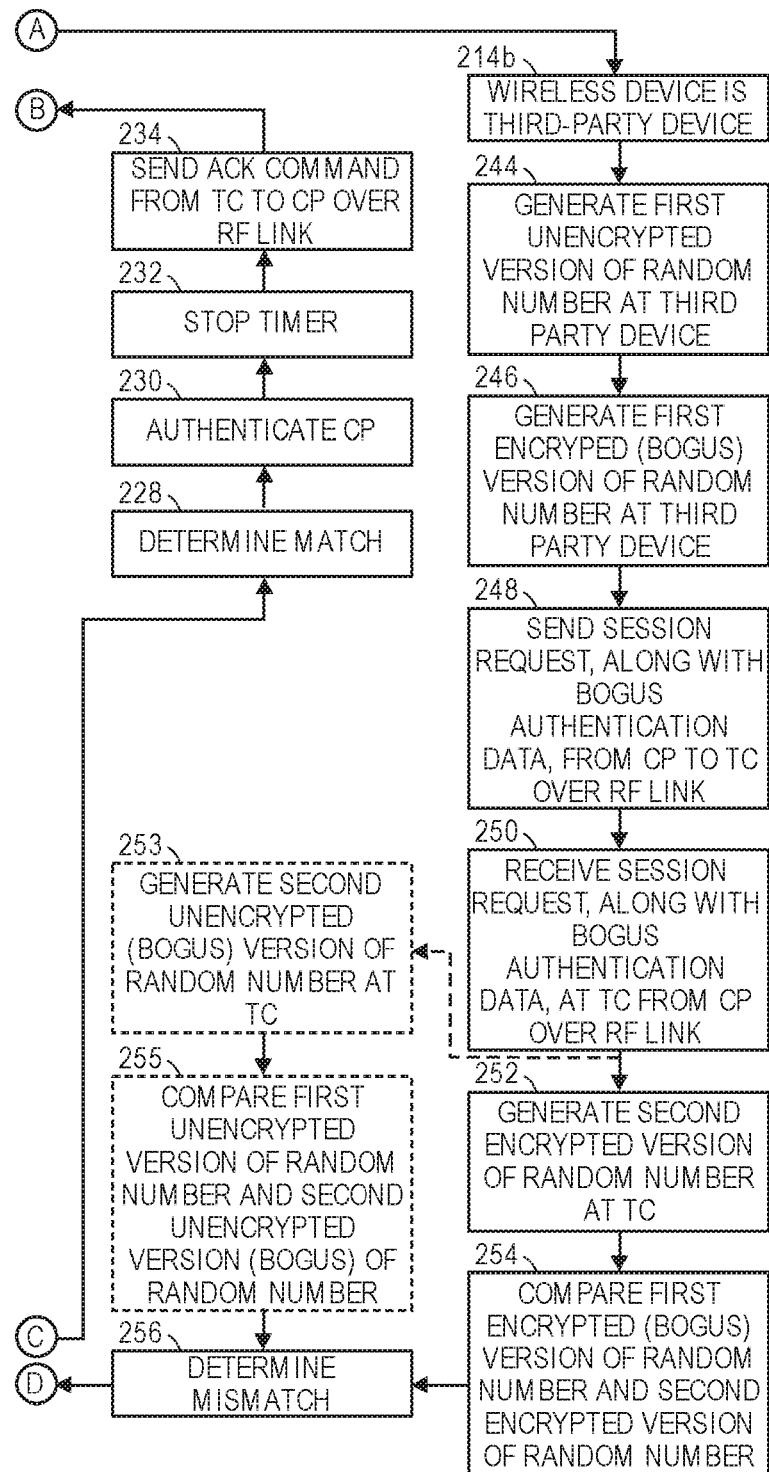

In the case where the TC 102 illustrated in FIG. 3 is used to authenticate a wireless device, another method 250 of authenticating a wireless device to the TC 102 will now be described with reference to FIGS. 3, 4, and 6. The method 250 is identical to the method 200 described with respect to FIG. 5, with the exception of turning the Bluetooth module 168 on in response to the manual triggering of the wireless actuator 120, and turning the Bluetooth module 168 off if the timer 178 indicates that the predetermined period of time has expired at step 208 or that the authentication procedure performed on the wireless device has failed at step 258, the wireless device can be prevented from commanding the TC 102 using any one of a variety of different techniques (step 211).

For example, the TC 102 may refuse to establish the RF communications link 118 with the wireless device only if the timer 178 indicates that the predetermined period of time has expired at step 208, and if the RF communications link 118 has already been established with the RF communications link 118, the RF communications link 118 may be terminated. In the illustrated embodiment, the communications driver software module executed by the microcontroller 158 of the TC 102 can instruct the Bluetooth module 168 to not establish the wireless communication link 118 in accordance with the Bluetooth protocol by, e.g., rejecting any request to connect from the wireless device, if the timer 178 indicates that the predetermined period of time has expired. If the wireless communications link 118 has been established in accordance with the Bluetooth protocol at step 212 prior to expiration of the predetermined period of time indicated by the timer 178, the communications driver software module executed by the microcontroller 158 may instruct the Bluetooth module 168 to terminate the wireless communications link 118 if the timer 178 indicates that the predetermined period of time has expired or if the wireless device (presumably, the third-party device 116) is not authenticated in accordance with the proprietary authentication procedure at step 258.

As another example, the TC 102 may ignore any commands received from the wireless device over the RF communications link 118 if the timer 178 indicates that the predetermined period of time has expired at step 208, or if the wireless device (presumably, the third-party device 116) is not authenticated in accordance with the proprietary authentication procedure at step 258. In the illustrated embodiment, the communications driver software module executed by the microcontroller 158 of the TC 102 can instruct the Bluetooth module 168 to not forward any commands received over the RF communications link 118, or to otherwise ignore any of such commands forwarded from the Bluetooth module 168 to the microcontroller 158.

The software modules described herein may be stored on a "computer readable storage medium" or "computer usable storage medium," which refers to any non-transitory medium that participates in providing instructions to a processor for execution. Such a medium may take many forms, including but not limited to, non-volatile media (e.g., optical or magnetic disks) and volatile media (e.g., dynamic memory).

Common forms of computer readable storage media includes, for example, electromechanical disk drives (such as a floppy disk, a flexible disk, or a hard disk), a flash-based, RAM-based (such as SRAM, DRAM, SDRAM, DDR, MRAM, etc.), or any other solid-state drives (SSD), a magnetic tape, any other magnetic or a magneto-optical medium, CD-ROM, any other optical medium, punch cards, paper tape, any other physical medium with patterns of holes, RAM, PROM, EPROM, FLASH-EPROM, any other memory chip or cartridge, or any other medium from which a computer can read. For example, the various forms of computer readable storage media may be used by the methods or the systems to store either temporarily or permanently information or data such as the one or more master regions, one or more master output layers, one or more global scratch layers, various transforms and inverse transforms, shapes, etc.

Although the authentication techniques have been described herein as being used to authenticate one wireless medical device (e.g., an external programmer) to another wireless medical device (e.g., a telemetry controller), the authentication techniques described herein can be used to authenticate any wireless device to another wireless device outside of the context of the medical field.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of communicating between a first device and a second device of a system over a wireless communications link, the method comprising:
   receiving a trigger signal in response to a user action;
   establishing a wireless communications link between the first device and the second device in response to the trigger signal;
   initiating an authentication procedure on the second device over the established wireless communication link;
   receiving a first unencrypted version of a random number and a first encrypted version of the random number from the second device over the wireless communications link; and
   performing an authentication procedure on the second device based on the first unencrypted version of the random number and the first encrypted version of the random number; and
   preventing the second device from commanding the first device to perform an action if the authentication procedure is not completed within a predetermined period of time after the wireless communication link has been established between the first device and the second device or if the authentication procedure fails within the predetermined period of time.

2. The method of claim 1, further comprising:
   storing a first encryption algorithm at the second device;
   generating the first unencrypted version of the random number;
   encrypting the first unencrypted version of the random number in accordance with the first encryption algorithm to generate the first encrypted version of the random number;
   transmitting the first unencrypted version of the random number and the first encrypted version of the random number over the wireless communication link;
   storing one of a second encryption algorithm and a decryption algorithm at the first device, the second encryption algorithm being identical to the first encryption algorithm, the decryption algorithm being complementary to the first encryption algorithm;
   wherein the authentication procedure is performed on the second device by respectively applying the one of the second encryption algorithm and a decryption algorithm to the first unencrypted version of the random number and the first encrypted version of the random number.

3. The method of claim 1, wherein the authentication procedure is performed by:
   generating a second encrypted version of the random number from the first unencrypted version of the random number;
   comparing the first and second versions of the encrypted random number; and
   determining if the first and second versions of the encrypted random number match.

4. The method of claim 1, wherein the authentication procedure is performed by:
   decrypting the first encrypted version of the random number to recover a second unencrypted version of the random number;
   comparing the first and second versions of the unencrypted random number; and
   determining if the first and second versions of the unencrypted random number match.

5. The method of claim 1, wherein the first unencrypted version of the random number and the first encrypted version of the random number are concurrently received from the second device over the wireless communications link.

6. The method of claim 1, further comprising receiving a session request from the second device over the wireless communications link, wherein the authentication procedure is performed in response to receiving the session request.

7. The method of claim 6, further comprising:
   sending an acknowledge command to the second device over the wireless communications link if the authentication procedure is successful; and
   in response to receiving the acknowledge command, sending commands from the second device to the first device over the wireless communications link to command the first device to perform the action.

8. The method of claim 6, further comprising sending a non-acknowledge command to the second device over the wireless communications link if the authentication procedure fails.

9. The method of claim 1, wherein the action is allowing modification of at least one operational parameter of the system.

10. The method of claim 1, wherein the wireless communications link has a range less of than one hundred feet.

11. The method of claim 1, wherein the wireless communications link is a radio frequency (RF) communications link.

12. The method of claim 11, wherein the RF communications link is a Bluetooth or a Wi-Fi communications link.

13. The method of claim 1, further comprising turning on a wireless communications module of the second device in response to the trigger signal, wherein the wireless communications link between the first device and the second device is established with the wireless communications module, and the second device is prevented from commanding the first device to perform the action by turning off the wireless communications module.

14. The method of claim 1, wherein the second device is prevented from commanding the first device to perform the action if the authentication procedure is not completed within the predetermined period of time.

15. The method of claim 1, wherein the second device is prevented from commanding the first device to perform the action by turning off the wireless communications module if the authentication procedure fails.

16. The method of claim 1, further comprising sending commands from the second device to the first device over the wireless communications link, wherein the second device is prevented from commanding the first device to perform the action by ignoring the commands received from the second device over the wireless communications link.

17. The method of claim 1, wherein the second device is prevented from commanding the first device to perform the action by terminating the wireless communications link.

18. The method of claim 1, wherein the first device is an external telemetry controller, and the second device is an external programmer, the method further comprising wirelessly communicating between the telemetry controller and at least one medical device implanted within a patient.

19. The method of claim 18, wherein the at least one medical device is implanted within a patient, and the telemetry controller is an external telemetry controller.

20. The method of claim 19, further comprising:

sensing physiological data of the patient with the at least one implanted medical device; and wirelessly transmitting the sensed physiological data from the at least one implanted device to the external telemetry controller.

21. The method of claim 20, further comprising controlling a bionic prosthesis based on the sensed physiological data.

22. The method of claim 21, wherein the bionic prosthesis is a bionic limb, the sensed physiological data is electromyogram (EMG) data, and controlling the bionic prosthesis comprises controlling movement of the bionic limb based on the sensed EMG data.

* * * * *